United States Patent [19]
Gresl

[11] Patent Number: 5,462,532
[45] Date of Patent: Oct. 31, 1995

[54] TROCAR WITH SAFETY SENSING SLEEVE

[75] Inventor: Charles Gresl, San Francisco, Calif.

[73] Assignee: Origin Medsystems, Inc., San Carlos, Calif.

[21] Appl. No.: 32,955

[22] Filed: Mar. 17, 1993

[51] Int. Cl.⁶ .................................................. A61B 17/34
[52] U.S. Cl. .......................................... 604/164; 606/185
[58] Field of Search ..................... 128/751, 754; 604/22, 23, 26, 164, 165, 169, 264; 606/1, 167, 170, 182, 184, 185

[56] References Cited

U.S. PATENT DOCUMENTS

| | | | |
|---|---|---|---|
| 4,419,094 | 12/1983 | Patel . | |
| 4,730,316 | 3/1988 | Desyllas et al. . | |
| 5,030,206 | 7/1991 | Lander | 606/185 |
| 5,066,288 | 11/1991 | Deniega et al. | 604/264 |
| 5,114,407 | 5/1992 | Burbank | 606/185 |
| 5,116,353 | 5/1992 | Green | 606/184 |
| 5,147,316 | 9/1992 | Castillenti | 606/185 |
| 5,152,754 | 10/1992 | Plyley et al. | 606/185 |
| 5,312,354 | 5/1994 | Allen et al. | 606/167 |

FOREIGN PATENT DOCUMENTS 344853  4/1973  U.S.S.R. .

*Primary Examiner*—Stephen C. Pellegrino
*Assistant Examiner*—Glenn Dawson
*Attorney, Agent, or Firm*—Timothy J. Lithgow; Heller, Ehrman, et al.

[57] ABSTRACT

A trocar assembly is provided wherein the obturator having a piercing tip and a sleeve around said obturator are housed within the trocar cannula. In the extended position the obturator tip and a portion of the distal end of the sleeve extend from the distal end of the cannula. During insertion of the obturator tip, sleeve and cannula into tissue, the force of tissue as the obturator penetrates the tissue which surrounds the exposed sleeve sensitizes the sleeve. At the proximal end of the sleeve a triggering mechanism is provided whereby upon release of the force of the sleeve at its distal end upon penetration through the tissue the sensitized sleeve releases to activate the triggering mechanism which retracts the obturator tip into the housing.

17 Claims, 4 Drawing Sheets

TROCAR WITH SAFETY SENSING SLEEVE

FIELD OF THE INVENTION

The present invention relates to trocars and, more particularly, to trocars incorporating means to shield the piercing tip of the obturator of the trocar after piercing through body tissue into a body cavity. In its more specific aspects, the present invention is concerned with a sensing sleeve which automatically activates retraction of the piercing tip into the trocar cannula after the leading edge of the sleeve penetrates through the body tissue.

BACKGROUND OF THE INVENTION

Trocars are pointed surgical instruments which puncture tissue to obtain access to body cavities. Inherent in such instruments is a danger that after the intended puncture, the piercing tip of the obturator (the removable shaft used to pierce the tissue) of the trocar will inadvertently puncture unintended tissue, vessels or organs.

Various techniques for avoiding this inadvertent puncturing are known in the prior art. In U.S. Pat. Nos. 4,601,710 and 4,654,050 the trocar obturator tip is shielded by a sleeve which extends around the point of the obturator after piercing is complete. This technique requires that something project beyond the piercing point of the obturator and requires the addition of a separate shielding element. U.S. Pat. Nos. 4,601,710 and 4,654,030 provide tubes which provide a passage extending into the body cavity after the obturator is removed. However, a shielding sleeve, in addition to these tubes, is required in these devices. This increases the bulk of the trocar and adds to the complexity of its mechanism.

U.S. Pat. No. 4,535,773 discloses the shielding of the piercing tip of an obturator of a trocar through either the interposition of an extensible shielding sleeve, or the retraction of the obturator into the cannula (the tube remaining in the incision after removal of the obturator). The latter arrangement relies upon a solenoid operated detent which holds an obturator in the extended position relative to the cannula and requires electronic sensing means in the tip of the obturator to activate the detent for release. This sensing means requires an electronic alarm network.

The present invention provides advantages over the devices discussed above in that the piercing obturator tip is retracted into a cannula upon completion of insertion of the trocar through the tissues of interest. However, a protecting sleeve extending beyond the end of the cannula into the cavity of the organ is not required.

SUMMARY OF THE INVENTION

The present invention provides a trocar assembly comprising an elongate obturator shaft having a piercing tip at its distal end, which is the end which is to be inserted into the body tissue. The proximal end is at the handle of the trocar. The trocar assembly further comprises an elongate tube housing accommodating the obturator shaft and a tubular sleeve mounted concentrically around the obturator shaft. The sleeve is axially movable relative to the obturator between a sensing position and a released position. The sleeve and shaft are also axially movable relative to the housing between a locked extended position wherein the piercing tip protrudes from the distal end of the housing, and a retracted position wherein the obturator is retracted into the housing. A first biasing means acts on the sleeve in its sensing position to counteract the force exerted on the distal end of the sleeve during penetration of the obturator shaft and sleeve through an orifice created by the piercing tip of the obturator. The sleeve is thus maintained in its sensing position during penetration through the body tissue. A second biasing means is on the obturator to move the obturator to its retracted position upon unlocking from its extended position. The trocar assembly also comprises a triggering means communicating with the sleeve and the obturator shaft, whereby upon penetration of the distal end of the sleeve through the orifice in the body tissue, the first biasing means causes the sleeve to move to its released position, thereby automatically causing the triggering means to unlock the obturator from its extended locked position and move to its retracted position by force of the second biasing means.

Therefore a principal object of present invention is to provide a trocar assembly which accommodates a sensing sleeve to sense penetration of the obturator tip through the body tissue and to automatically retract the obturator tip into the trocar housing upon completion of penetration.

A further object of the invention is to provide a trocar which has an automatically retracting obturator tip upon completion of the intended puncture, without the requirement of electronic sensors.

Another object of the invention is to provide a trocar assembly wherein the shielding function is automatic and achieved in a simple manner which requires no special expertise on the part of the user.

Another object of the invention is to provide a simplified mechanism to retract a trocar obturator tip into the cannula within which it is received, after the trocar obturator tip has penetrated through the tissue and there is no longer any force being applied to the trocar by resistance to the penetration.

These and other objects will be more apparent when viewed in light of the following detailed description and accompanying drawings and claims.

BRIEF DESCRIPTIONS OF THE DRAWING

DESCRIPTION OF THE PREFERRED EMBODIMENTS

It will be realized that all of the embodiments disclosed herein provide the improvement whereby a sleeve senses the release of pressure after penetration through the tissue, rather than the tip of the obturator. According to the present invention when the pressure is released on the sensing sleeve, since the tip of the obturator precedes the sensing sleeve through the tissue, it is clear that the tip of the obturator has already entered into the body cavity through the tissue and that the orifice has been made completely through the tissue. This is an advantage over retracting tip trocars wherein the sensing of penetration is performed by the tip of the obturator. When the tip of the obturator is used as the sensor, sometimes the pressure release at the tip of the obturator is sufficient to trigger the retraction mechanism prior to full penetration of the tip through the tissues, thus leaving incomplete penetration into the body cavity. According to the present invention, even if the pressure release at the leading edge of the sensing sleeve is sufficient to trigger the retraction mechanism prematurely prior to entry of the sleeve into the body cavity, since the obturator tip precedes the sleeve into the body cavity, full penetration of the tissues has already occurred. Therefore, even with premature firing complete penetration by the obturator is attained.

As an additional advantage, the tuning of the tension of a trocar with the sensing sleeve is made easier to accomplish than the tuning of the sensing mechanism of a retracting tip trocar which uses the obturator tip as a sensor. In the former case of a sensing sleeve, the sleeve is a separate piece from the obturator so the sensing and retraction function take place on different pieces. In the latter case, the obturator must be tuned for retraction and cocking (for the retraction function), and for sensing and triggering (for the sensing function).

Figure 1:
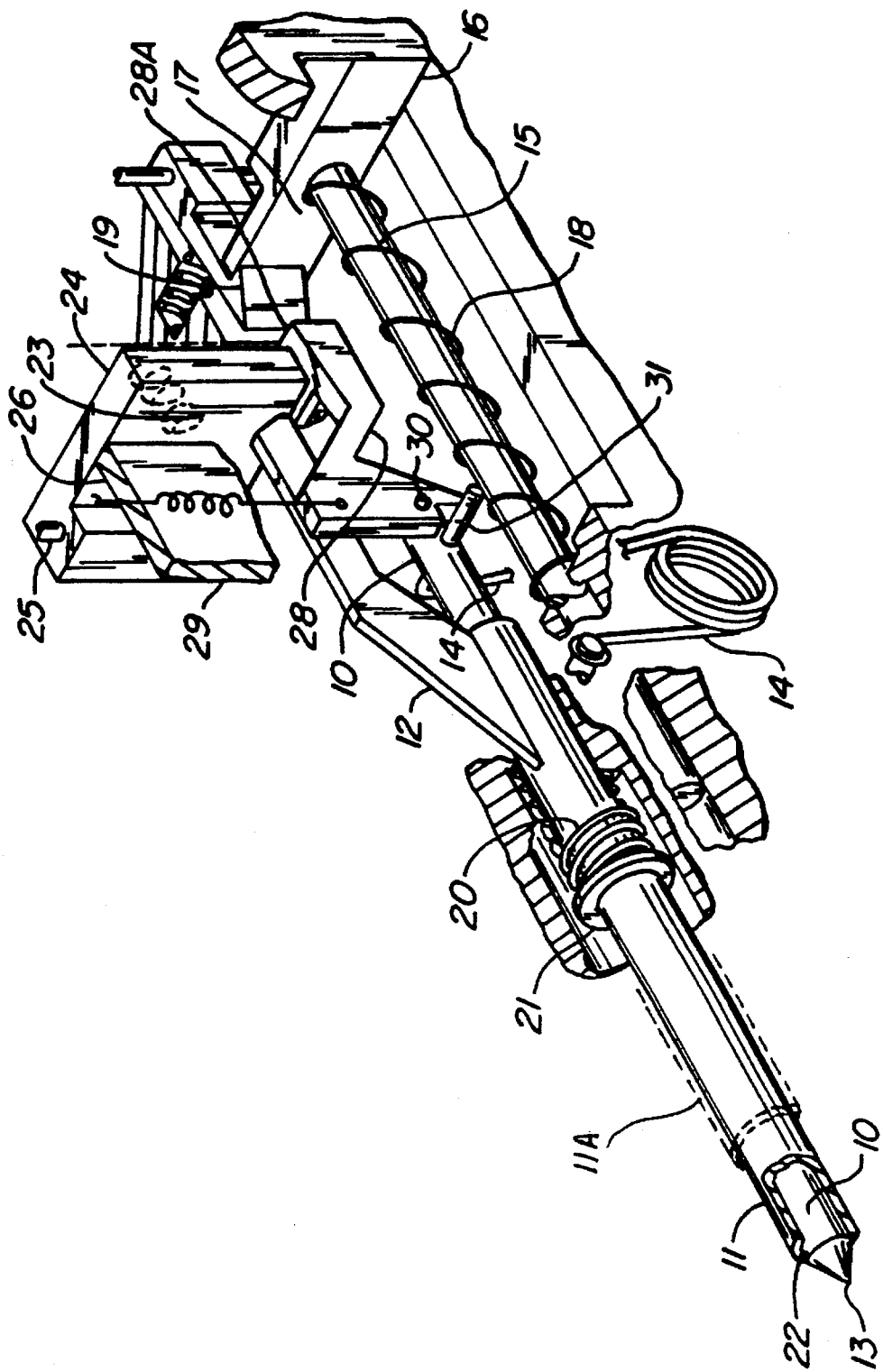
FIG. 1 is a perspective of a preferred embodiment of a trocar according to the invention.
Figure 1A:
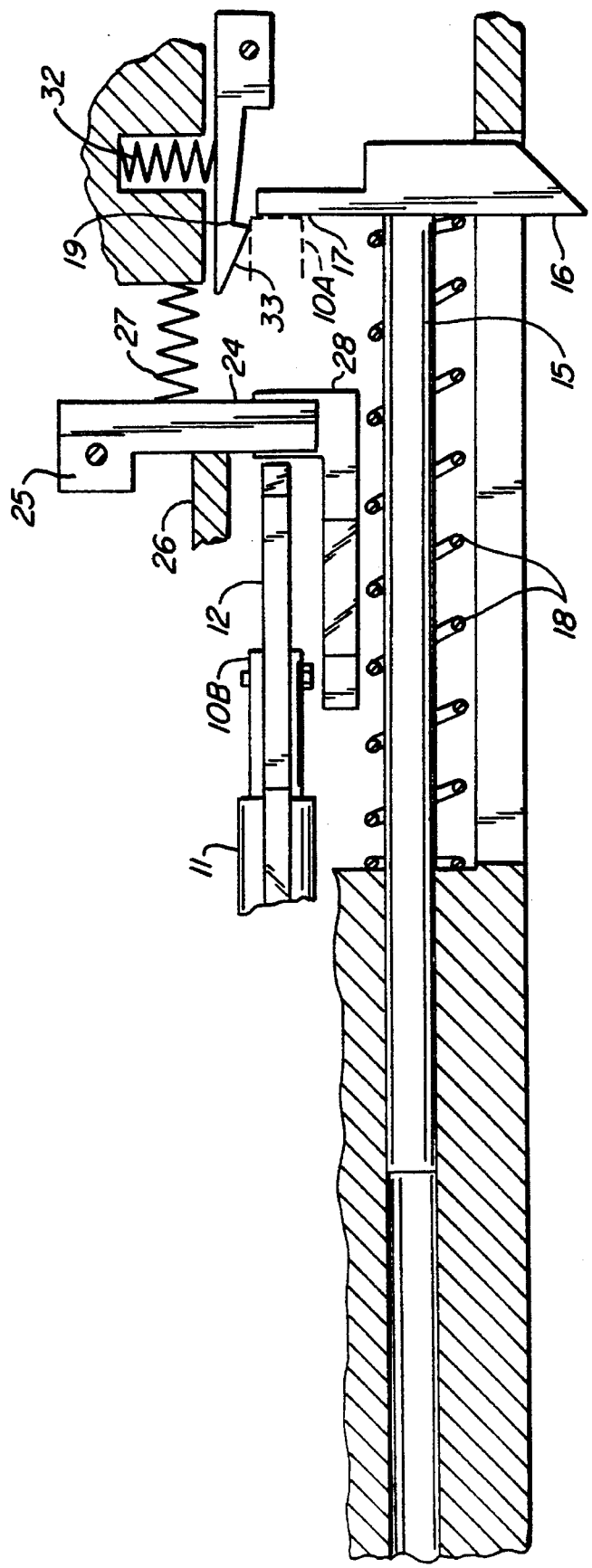
FIG. 1A is a schematic illustration of the detail of the cocking mechanism of the trocar in FIG. 1.

A preferred trocar device according to the present invention is shown in FIG. 1 and FIG. 1A. The trocar comprises an obturator 10 and a sleeve 11, both of which are shown in a shorter length than required for use in order to facilitate description. The distal end of the cannula 11A around the sleeve 11 is shown in shadow but a complete housing surrounding the cocking and triggering mechanisms is not shown for purpose of clarity of the drawing. The sensing sleeve 11 is connected to and moves axially with arm 12. The obturator 10 with its piercing tip 13 at its distal end is located concentrically within the sleeve 11. At the proximal end of the obturator 10 it is connected to a biasing spring 14 which is shown in FIG. 1 in its tensioned position.

FIG. 1A is a schematic partial side view of the device shown in FIG. 1 to more clearly show how the cocking arm 15 is used to move the obturator 10 to its cocked position. Referring to FIG. 1A, before obturator 10 is cocked, it is in a safety position as shown by the shadow line 10A wherein its proximal end abuts against surface 17 of the cocking slide 15. The locking arm 19 is disengaged but is tensioned to move in a downward direction by tensioning spring 32. In this position arm 19 abuts against the obturator when it is in position 10A. Upon movement of the cocking arm 16 in a distal direction and against spring 18, the surface 17 moves the obturator 10 in a distal direction against the tensioning spring 14 (for the obturator 10) and tensioning spring 18 (for sliding arm 15). The obturator 10 is cocked when pin 31 slides over the beveled edge on trigger arm 28, allowing trigger arm 28 to pivot around its pivot 30 until pin 31 slips to a position forward of trigger arm 28 and achieves a cocked position when the trigger arm 28 returns under tension of spring 29. After this cocking has occurred, release of handle 16 allows the slide 15 to return to its rearward position under tension of spring 18 whereby it slides across the beveled edge 33 on locking arm 19 into its locked position as shown in FIG. 1. This prevents inadvertent movement of the cocking arm 16 during use of the trocar after the obturator has been cocked.

As shown in FIG. 1, the obturator 10 is in its cocked position, having been cocked by use of cocking slide member 15 which is manipulated external to the housing of trocar handle by way of cocking handle 16. The cocking slide 15 is used in a manner such that the face 17 contacts the proximal end of obturator 10 when slide 15 is moved in the distal direction. After the obturator 10 is locked in its cocked position, the cocking slide 15 returns to the rearwardly locked position (as shown in FIG. 1) under tension of spring 18. Once cocking slide 15 is used to arm the obturator 10, it is locked in its rearward position by locking plate 19.

As shown in FIG. 1 the sleeve 11 is ready for insertion into body tissue, so any movement in the proximal direction of the sleeve 11 will be against the biasing spring 20 by virtue of contact of the biasing spring 20 against retention ring 21 which is attached to the sensing sleeve 11.

The sensing sleeve trocar operates as follows. From its cocked position shown in FIG. 1, the obturator tip 13 (extending from the cannula 11A) is pushed through the body tissue by the user as the leading edge 22 (also extending from the cannula 11A) of the sensing sleeve enters through the orifice caused by the obturator 10 through the tissue. Pressure against edge 22 and sides of the exposed sleeve 11 causes sleeve 11 to move slightly in a proximal direction against the tensioning spring 20. The spring rate on the tensioning spring 20 is such that it will counteract some of the force applied at the distal end of the sleeve 11 by the tissue during penetration of the obturator 10 but the tensioning force will not be sufficient enough to prevent movement of the sleeve 11. Accordingly, there will be a float distance which is allowable of sleeve 11 during penetration of the obturator so that a slight release of force upon the obturator by the user during penetration will not trigger the release of the obturator. However the force on tensioning spring 20 is sufficient to allow the sleeve 11 to move in a proximal direction during penetration through the tissue such that the proximal end 23 of the arm 12 will gradually displace locking plate 24 which pivots around pin 25. Motion of plate 24 in the distal direction is impeded by abutment against fixed plate 26. Plate 24 is biased to hold its position against plate 26 by biasing spring 27 which is more clearly shown in FIG. 1A. Plate 24 initially retains trigger arm 28 in the locking position and is replaced in that function by arm 12 during insertion of the obturator through tissue. Trigger arm 28 is biased by spring 29 to abut initially against the bottom surface of plate 24 and then against the bottom surface of arm 12 during insertion of the obturator.

Just prior to complete penetration of the obturator 10 and the leading edge 22 of sleeve 11 into the body cavity, when there is still force being applied against sleeve 11 by the body tissue, arm 12 will be in its rearward position and plate 24 will be rotated away from retaining plate 26 and clear of trigger arm 28. Trigger arm 28 will then be held in its locked position only by arm 42. After plate 24 has cleared arm 28, a slight clearance between the bottom surface of arm 12 and the upper surface of arm 28 allows arm 28 to pivot upwardly under force of spring 29 until contact is made with arm 12. The slight movement prevents plate 24 from pivoting forward again since it is impeded by abutment against surface 28A on arm 28. Then immediately upon penetration of the leading edge 22 of sleeve 11 into the body cavity, when the force against sleeve 11 is released, the sleeve 11 and arm 12 are forced forward under the force of tensioning spring 20. This momentarily frees the upper of surface of triggering arm 28 allowing it to pivot upwardly about its axis of attachment at 30 thereby freeing the pin 31 attached to the obturator 10. Upon release of pin 31 the obturator 10 moves in a proximal direction under tension of spring 14, thus retracting it into the cannula 11A. When obturator 10 retracts in this manner, sleeve 11 has moved slightly in the distal direction during the triggering motion, but sleeve 11 is not retracted along with the obturator 10. When there is a sufficient displacement of obturator 10 during this retraction motion (which can be attained by selecting an appropriate location for pin 31 on the proximal end of obturator 10), then obturator 10 also retracts into the sleeve 11.

As shown in FIGS. 1 and 1A, the triggering mechanism wherein the motion of the sensing sleeve 11 is used to trigger release of the obturator 10 is shown by the components 12, 24, 28, 31 and their corresponding biasing springs.

Figure 2:
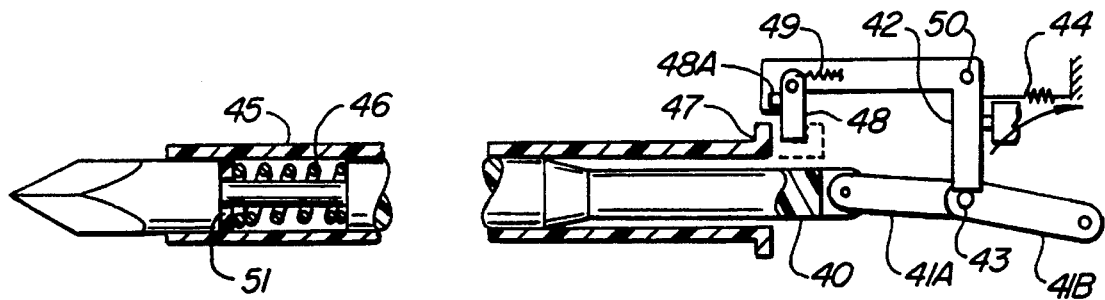
FIG. 2 is an illustration of another embodiment of a triggering mechanism for a trocar according to the invention.

Other mechanisms may be utilized to attain triggering. For example, referring to FIG. 2, the obturator 40 may be retracted by means of folding arms 41A and B which are appropriately biased by tensioning means (not shown). In the cocked position, as shown, the arms 41A and B are prevented from folding (to retract the obturator) by engagement of a surface of trigger 42 against pin 43. Trigger 42 is biased by spring 44. Upon motion of sleeve 45 in a proximal direction against tensioning spring 46 the proximal end 47 of sleeve 45 displaces latch 48 which is under tension of spring 49, by rotation in a counterclockwise direction. The proximal end 47 is then in a position (shown by the shadow line) to trigger retraction of the obturator. When sleeve 45 moves from this position in a distal direction, end 47 contacts latch 48 (which cannot rotate in a clockwise direction against stop 48A). This forces release trigger 42 to rotate about its axial pivot 50 in a clockwise direction thereby disengaging pin 43 and allowing arms 41A and 41B to fold to retract the obturator 40. In FIG. 2 (and FIG. 5), the obturator 40 and sleeve 45 retract together in the same motion because plate 51 impedes axial motion of the obturator in the proximal direction independent of the sleeve 45. This is in contrast to the embodiment shown in FIG. 1 wherein the obturator 10 can retract into sleeve 11.

Figure 3:
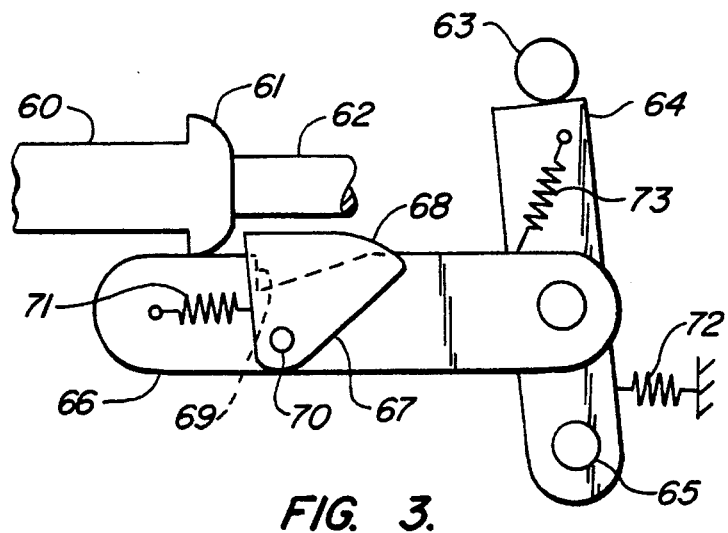
FIGS. 3, 4 and 5 illustrate alternative triggering mechanisms for a trocar according to the invention.

Referring to FIG. 3, there is shown an alternative triggering mechanism. Only the components of the triggering mechanism are shown. The obturator 62 is connected to a double arm mechanism similar to that shown as 41A and 41B in FIG. 2 and the pivot 63 is a pivot joint corresponding to 43 in FIG. 2. In FIG. 3 the sleeve 60 has a flanged distal end 61. As shown the obturator is in a cocked position, held in place by retaining arm 64. During the cocking movement of the obturator the retaining arm 64 moves in a clockwise direction around its pivot 65. During this motion arm 66 travels in a generally proximal direction. Therefore guard 67 is provided so that during the cocking motion the flanged end 61 of the sleeve slides over the ramp 68 on guard 67 to avoid engagement with the notch 69. The guard 67 pivots around its pivot 70 and is under the tension of spring 71. Arm 64 is under tension of spring 72 and the arm 66 is under the tension of spring 73. As shown the triggering mechanism is in the position with the obturator cocked and the sleeve 60 in position prior to insertion of the obturator into the body tissue.

While the obturator is being inserted through the tissue the following action occurs. During insertion the pressure on the leading edge of the sleeve 60 slowly moves the flange 61 in a proximal (rearward) direction toward the notch 69. The sleeve 60 is under tension of a spring (not shown) similar to that shown in FIG. 2, item 46. As the flange 61 moves in a proximal direction it displaces the guard 67 and eventually becomes engaged with the notch 69 and interlocks therewith. When the leading edge of the sensing sleeve 60 clears the tissue and the pressure on the sleeve is released by the body tissue, the sleeve 60 moves forward in the distal direction. Since, at this point, the flange 61 and the notch 69 are interlocked, the arm 66 is also pulled in a forward direction which in turn pulls arm 64 in the forward direction to disengage pin 63. The disengagement of pin 63 fires the obturator and retracts it into the cannula (not shown) at the distal end.

Figure 4:
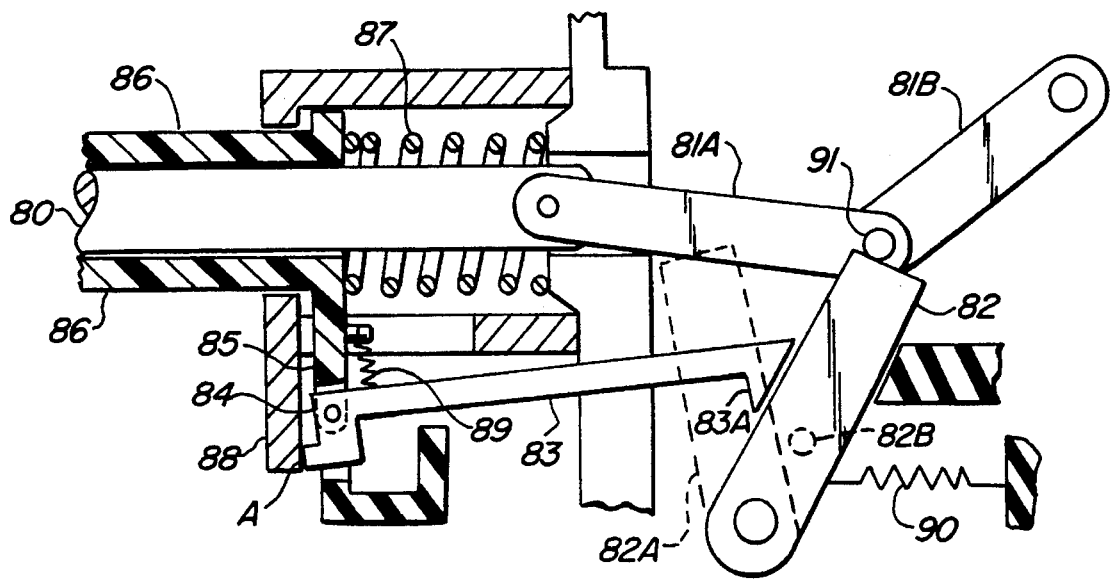

Referring to FIG. 4 there is shown yet another embodiment of a triggering mechanism. Referring to FIG. 4 the obturator 80 at its proximal end is shown in a cocked position whereby folding arms 81A and 81B are held in place by retaining arm 82. Lever 83 is attached through its pivot 84 to a flange 85 on the proximal end of the sleeve 86. Lever 83 is aligned so that notch 83A can engage pin 82B on arm 82. Sleeve 86 is tensioned by spring 87. The tensioning means on the obturator is not shown. As the sensing sleeve 86 is deflected in the proximal direction (to the right as shown) against the force of spring 87 during insertion of the obturator, lever 83 is disengaged at point A from the wall 88. This allows the lever 83 to pivot in a clockwise direction under the force of spring 89, while moving in the proximal direction (to the right, in FIG. 4). This motion allows the bottom surface of arm 83 to engage pin 82B. As the tissue pressure on the distal end of the sleeve 86 is reduced, flange 85 moves in the distal direction (to the left, in FIG. 4), whereby notch 83A engages pin 82B, causing arm 82 to rotate counterclockwise. This disengages pin 91 and allows the obturator 80 to be retracted into the cannula (not shown) at the distal end of the trocar. When arm 83 contacts wall 88 at point A, arm 83 is rotated counterclockwise, freeing pin 82B. This allows arm 82 freedom of rotation during action during cocking of obturator 80 by unfolding arms 81A and 81B.

Figure 5:
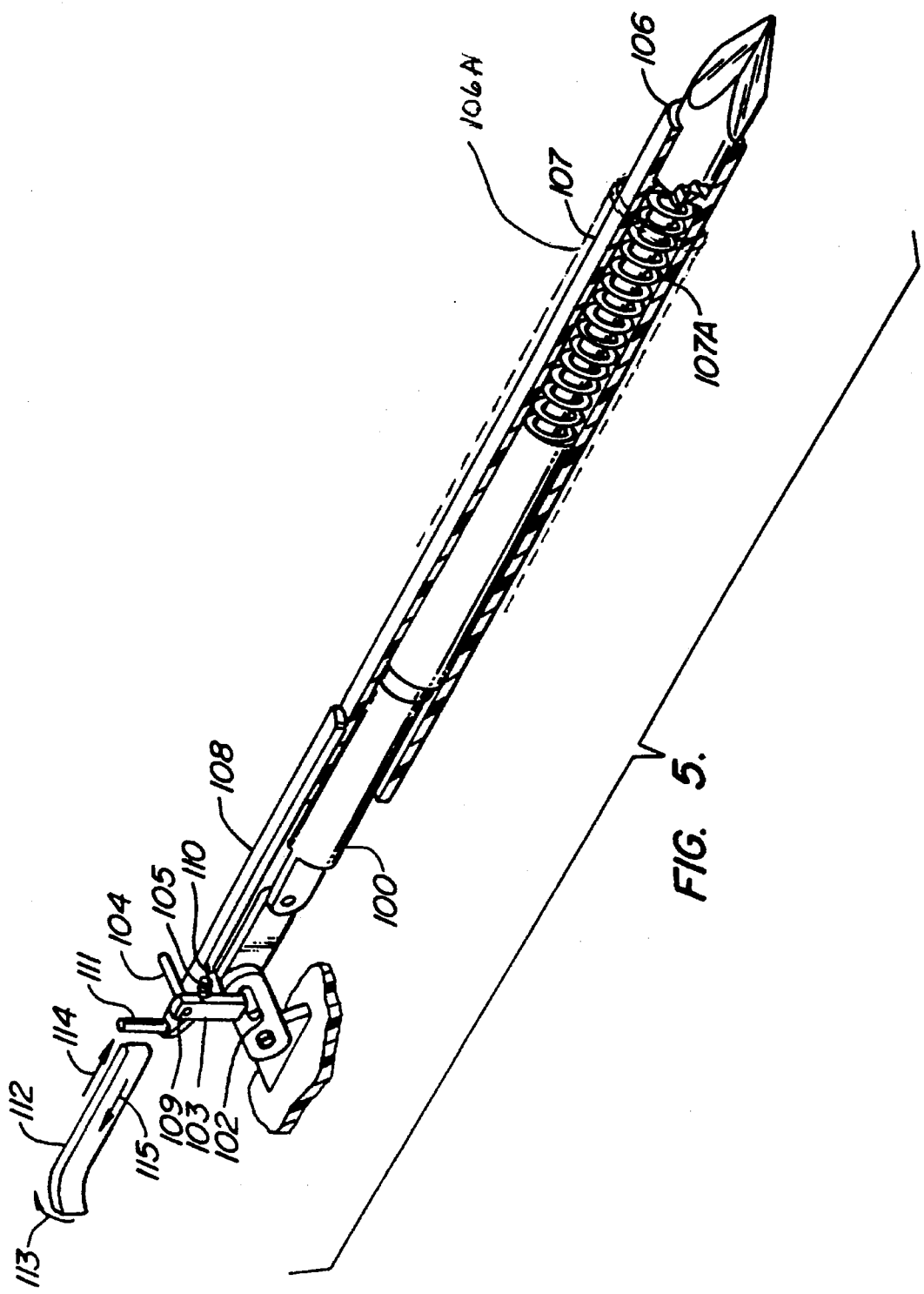

In FIG. 5 there is shown yet another embodiment of a triggering mechanism. As shown the obturator 100 is in a cocked position. The tensioning means on the folding arms 101A and 101B is not shown. The obturator 100 is shown in a cocked position by engagement of pin 102 against latch 103 which pivots around its pivot 104 under the force of spring 105. During insertion of the obturator 100 into the tissue the leading edge 106 of sleeve 107 encounters the force of the tissue and is moved in a rearward (proximal) direction against tensioning spring 107A together with arm 108. As arm 108 moves in a rearward direction it is tensioned in a lateral direction against latch 103 by slippage of latch 103 against the beveled surface 109 at the proximal end of arm 108. After arm 108 is sufficiently displaced, notch 110 engages the rear edge of latch 103. Upon penetration of the obturator and leading edge 106 of sleeve 107 through the tissue the force on the sleeve 107 exerted by the tissue is released and the sleeve 107 moves forward in a distal direction. This motion trips latch 103 which disengages pin 102 and fires both sleeve 107 and obturator 100 in a proximal direction thereby retracting them into the cannula 106A, shown in shadow, at its distal end.

The purpose of pin 111 attached at the extreme proximal end of arm 108, and the camming plate 112 is to allow slot 110 to clear arm 103 during the cocking of the obturator 100 and sleeve 107. Since sleeve 107 and obturator 100 are cocked together, the notch 110 must avoid engagement with arm 103 as arm 108 is moved forward to be locked in the cocked position. Therefore, during the cocking motion pin 111 slips along the inner edge of camming plate 112 beginning at arrow 113 and continuing along arrow 114. During traverse of pin 111 along this surface the arm 108 is tensioned in a lateral direction so that notch 110 clears the latch 103. After the cocking motion is completed the pin 111 clears the distal end of plate 112 and arm 108 is relaxed, whereby pin 111 is juxtaposed to slide unobstructed along the opposite side of plate 112 as shown by arrow 115.

From the foregoing detail of the preferred embodiments it is apparent that the invention enables the attainment of the objects initially set forth herein. In particular, the invention provides a trocar which instantaneously retracts to a shielded position upon completion of the penetration of tissue.

It should be appreciated that the invention is not intended to be limited by the specific details of the embodiments illustrated and described herein, but rather is defined by the accompanying claims.

What is claimed is:

1. A trocar assembly comprising:

a cannula having a distal end and a proximal end, a handle at the proximal end of said cannula, and an elongate obturator within said cannula having a distal end, said elongated obturator having a piercing means at its distal end;

a sleeve mounted concentrically around said obturator and being axially movable relative to said obturator between a sensing position and a released position;

wherein said obturator being axially movable relative to said cannula between a locked extended position wherein said piercing means of said obturator protrudes from said distal end of said cannula, and a retracted position wherein said obturator is retracted into said cannula;

triggering means communicating between said sleeve and said obturator to unlock said obturator from said extended position upon movement of said sleeve from said sensing position to said released position;

a first biasing means acting on said sleeve in said sensing position to counteract force exerted at a distal end of said sleeve during penetration of said obturator and sleeve through an orifice created by said piercing means in body tissue to thereby maintain said sleeve in said sensing position during penetration while allowing slight motion of said sleeve in the proximal and distal directions without releasing said triggering means when said obturator is in said locked extended position; and second biasing means on said obturator to move said obturator to said retracted position upon unlocking said obturator from said extended position.

2. A trocar assembly according to claim 1 wherein said obturator and sleeve are axially movable together relative to said cannula between said extended position and said locked position and said sensing position and said released position, respectively, by force of said second biasing means.

3. A trocar assembly according to claim 2 further comprising a cocking means for moving said obturator and sleeve to said locked extended position and said sensing position, respectively.

4. A trocar assembly according to claim 1 wherein said triggering means comprises activating means attached to a proximal end of said sleeve and latching means holding a proximal end of said obturator in said extended position.

5. A trocar assembly according to claim 4 wherein said activating means comprises an arm extending from said proximal end of said sleeve.

6. A trocar assembly according to claim 4 wherein said activating means comprises a flange on said proximal end of said sleeve.

7. A trocar assembly according to claim 4 wherein said latching means comprises a pin on said obturator and retaining means engaged with said pin.

8. A trocar assembly according to claim 4 wherein said latching means comprises two foldable pivoting arms, one end of one of said arms being pivotably attached to the proximal end of said obturator, a pin at a pivot point connecting said arms, and retaining means engaged with said pin.

9. A method for inserting a trocar through body tissue into a body cavity, said trocar comprising a hollow cannula having a distal end for insertion through said tissue, an obturator having a distal end with a tissue-piercing tip axially movable within said cannula between a locked extended position wherein said piercing tip of said obturator protrudes from said distal end of said cannula, and a retracted position wherein said obturator is retracted into said cannula, a sensing sleeve mounted concentrically around said obturator and being axially movable relative to said obturator between a sensing position and a released position, triggering means communicating between said sleeve and said obturator to unlock said obturator from said extended position upon movement of said sleeve from said sensing position to said released position, a first biasing means acting on said sleeve in said sensing position to counteract force exerted at the distal end of said sleeve during penetration of said obturator and sleeve through an orifice created by said piercing tip in body tissue to thereby maintain said sleeve in said sensing position during penetration while allowing slight motion of said sleeve in the proximal and distal directions without releasing said triggering means while said obturator is in said locked extended position, and a second biasing means on said obturator to move said obturator to said retracted position upon unlocking said obturator from said extended position comprising the steps of:

inserting said piercing tip and said sensing sleeve into said tissue while moving said sleeve to said sensing position with an allowable slight motion of said sleeve in the proximal and distal directions not releasing said triggering means, piercing through said tissue into said body cavity with said piercing tip, moving said sleeve to said released position, and retracting said piercing tip into said cannula.

10. A trocar comprising an elongate obturator having a distal end and a proximal end and piercing means at its distal end;

a sleeve mounted concentrically around said obturator and being axially movable relative to said obturator between a sensing position and a released position;

said obturator being axially movable relative to said sleeve between an extended cocked position and a retracted position wherein said obturator is cocked in said extended position for release to said retracted position;

triggering means communicating between said sleeve and said obturator to release said obturator from said extended cocked position upon movement of said sleeve from said sensing position to said released position;

a first biasing means acting on said sleeve in said sensing position to counteract force exerted at a distal end of said sleeve during penetration of said obturator and sleeve through an orifice created by said piercing means in body tissue to thereby maintain said sleeve in said sensing position during penetration while allowing slight motion of said sleeve in the proximal and distal directions without releasing said triggering means when said obturator is in said extended cocked position; and second biasing means on said obturator to move said obturator to said retracted position upon releasing said obturator from said extended cocked position.

11. A trocar according to claim 10 wherein said obturator and sleeve are axially movable together between said extended cocked position and said retracted position and said sensing position and said released position, respectively, by force of said second biasing means.

12. A trocar according to claim 11 further comprising a cocking means for moving said obturator and sleeve to said locked extended position and said sensing position, respectively.

13. A trocar according to claim 10 wherein said triggering means comprises activating means attached to a proximal end of said sleeve and latching means holding the proximal end of said obturator in said extended cocked position.

14. A trocar according to claim 13 wherein said activating means comprises an arm extending from said proximal end of said sleeve.

15. A trocar according to claim 13 wherein said activating means comprises a flange on said proximal end of said sleeve.

16. A trocar according to claim 13 wherein said latching means comprises a pin on said obturator and retaining means engaged to said pin.

17. A trocar according to claim 13 wherein said latching means comprises two foldable pivoting arms, one end of one of said arms being pivotably attached to the proximal end of said obturator, a pin at a pivot point connecting said arms, and retaining means engaged to said pin.

* * * * *